United States Patent [19]

Smith

[11] 4,323,849
[45] Apr. 6, 1982

[54] COULOMETER
[75] Inventor: Stephen H. Smith, Playa del Rey, Calif.
[73] Assignee: Hybricon, Inc., North Hollywood, Calif.
[21] Appl. No.: 111,261
[22] Filed: Jan. 11, 1980
[51] Int. Cl.³ ............................................. G01N 27/42
[52] U.S. Cl. .................................... 324/428; 324/434
[58] Field of Search ................ 324/425, 427, 428, 434

[56] References Cited
U.S. PATENT DOCUMENTS
4,193,026 3/1980 Finger et al. ........................ 324/428

Primary Examiner—Michael J. Tokar
Attorney, Agent, or Firm—Lyon & Lyon

[57] ABSTRACT

An improved coulometer is disclosed wherein a precision amplifier and integrator section provide to a logic section and a detector section a signal representative of charge provided to or from one or more storage batteries. When the integrator output reaches a predetermined threshold, the detector section causes a threshold signal to be generated which in turn generates a signal to reset the integrator and increment or decrement a counter. The output of the counter corresponds to ampere-hours of available charge and may be displayed as well as used to determine whether to continue charging or other control functions. Errors are minimized through the use of temperature compensation and fine adjustment circuits. In addition, alternate cycles of the input to the integrator logic are inverted to prevent errors due to offset voltages, drift and imbalance in detection circuits from being cumulative.

15 Claims, 2 Drawing Figures

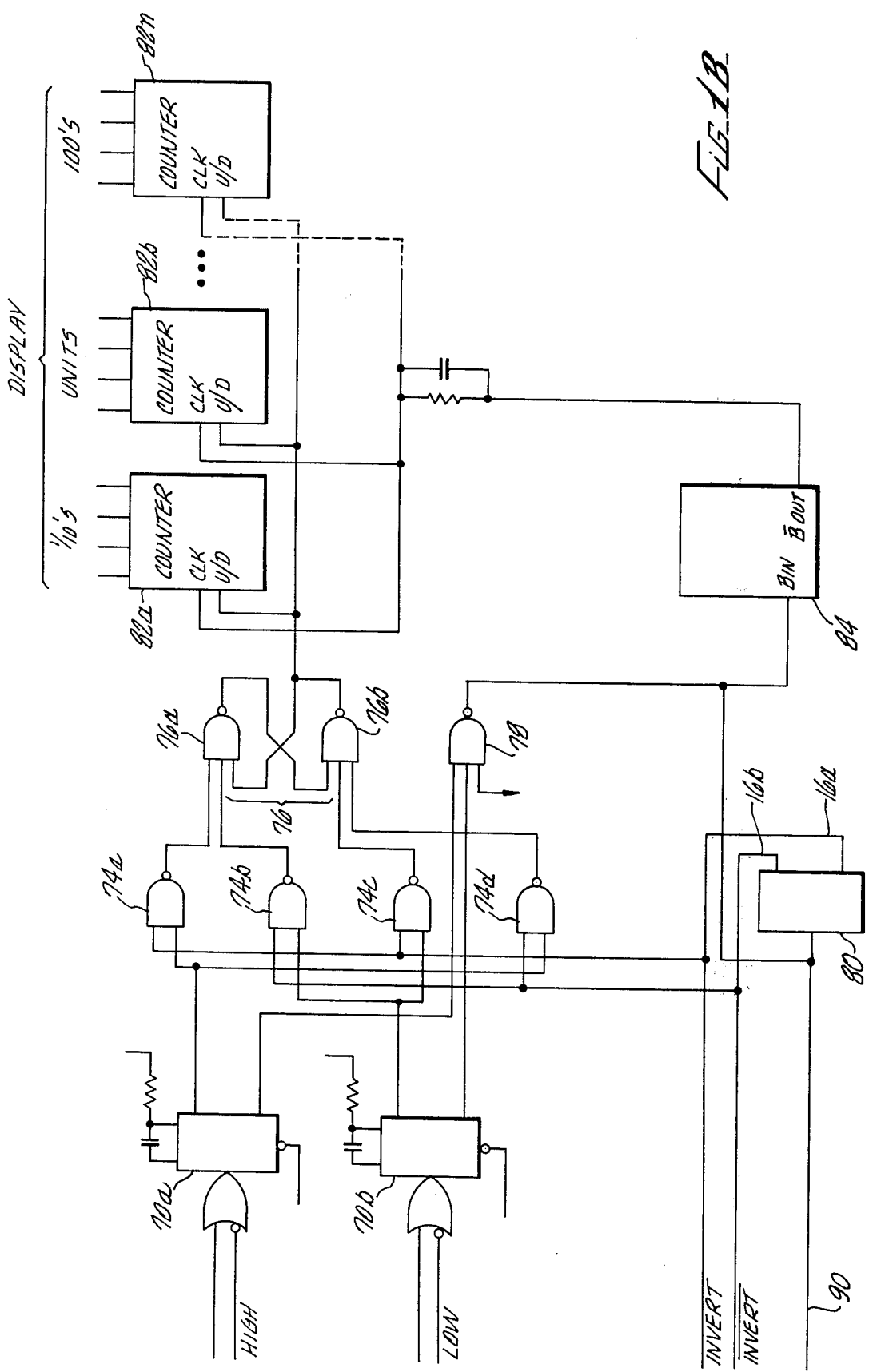

COULOMETER

FIELD OF THE INVENTION

The present invention relates generally to devices for measuring electrical charge, or ampere-hour meters, and more particularly to devices for monitoring the current delivered to or from a storage battery during charging. The present invention finds particular application to electric vehicles which employ rechargeable storage batteries as a power source.

RELATED APPLICATIONS

This application is related to the application of Stephen H. Smith enitled High Speed Non-Saturating Inverter and the application of Robert G. Metzner and Stephen H. Smith entitled Hybrid Electric Vehicle Control Methods and Devices, both filed concurrently herewith.

BACKGROUND OF THE INVENTION

Many devices are well-known in the prior art for measuring the capacity or remaining charge of various types of storage batteries. For batteries having a liquid electrolyte, an hydrometer has found application since it provides a display of specific gravity of the electrolyte, which is generally proportional to remaining charge. However, measurement of specific gravity is of limited usefulness because the density of the electrolyte near the top of the cell frequently differs from the density near the plates. In addition, diffusion must take place over time, and thus as much as twenty-four hours may be required for accurate measurement using this approach. Still further, the temperature of the electrolyte must be known for accurate measurement.

Other devices for measuring storage capacity have involved measurement of battery terminal voltages, for example using an expanded scale near the top of the voltage range. However, voltage is dependent upon the state of the electrolyte, and thus this approach suffers from each of the limitations inherent in monitoring the electrolyte itself. In addition, voltage at the battery terminals must be measured under no load/no charge conditions, and thus requires that all charging or load circuits be disconnected during measurement. If such circuits cannot be disconnected, battery impedance must be considered, which results in complex compensation circuits. Wattmeters are subject to similar limitations.

SUMMARY OF THE INVENTION

The present invention improves upon the performance of prior ampere-hour and charge storage devices, since the indication of charge is independent of voltage and battery characteristics, and also because circuit and environmentally induced errors are substantially reduced or eliminated. The apparatus of the present invention is supplied a shunt signal representative of current supplied by or to the battery or batteries.

The charging signal is then supplied, through analog switches, to a precision amplifier and an integrator, where the signal is accumulated until a predetermined threshold is reached. The threshold is set by a detection circuit and indicates that a quantum of charge has been supplied to the batteries.

Once the charge storage threshold is reached, the integrator output is used to generate an increment or decrement signal to a counter, and is reset to begin a new cycle of charge accumulation. Depending upon whether the batteries are being charged or depleted, the counter is incremented or decremented. The counter output is then provided to a suitable display as an indication of stored charge. An aspect of the present invention includes an arrangement for using a three and one half bit display to provide four digit resolution.

To minimize thermally induced errors, as well as other circuit errors, the input signal to the integrator is inverted on alternating counts by means of circuitry driven by the threshold detection circuitry. The inversion signal is supplied to a complementary arrangement of the aforementioned analog switches, causing the polarity of the signal supplied to the precision amplifier and the integrator to be reversed. Thus errors resulting from thermal or other offsets or imbalances, all of which tend to be of a single polarity, are substantially avoided.

It is thus one object of the present invention to provide an improved ampere-hour monitor.

It is another object of the present invention to provide a coulometer having improved accuracy.

It is a further object of the present invention to provide an improved coulometer in which the input signal is inverted on alternate cycles to minimize error.

These and other objects of the present invention can be better appreciated from the following detailed description of the invention, in which FIGS. 1A and 1B are schematic diagrams of the monitoring circuitry of the present invention.

DETAILED DESCRIPTION OF THE INVENTION

Figure 1A:
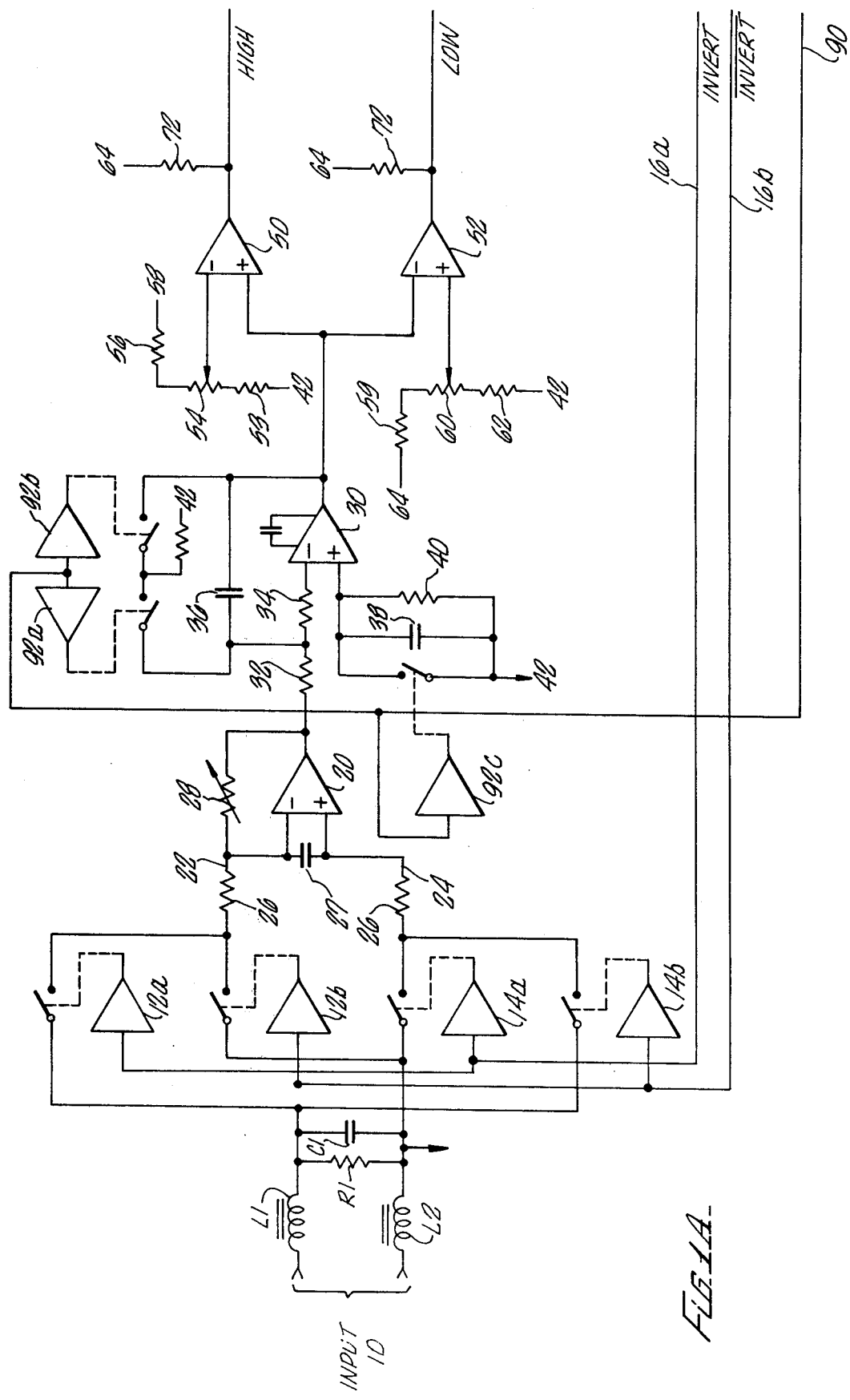

Referring to FIGS. 1A and 1B, which reflect the circuitry for one embodiment of the present invention, a shunt signal is provided at a pair of input terminals 10. The input signal will preferably be a DC signal proportional to the current through the shunt (not shown), wherein the polarity reflects the direction in which the current is flowing through the shunt. A pair of inductances L1 and L2 and a resistor R1 and capacitor C1 provide impedance matching.

The shunt signal is then supplied to a plurality of solid state switches, which are grouped into pairs 12a and 14a and 12b and 14b. The solid state switches 12a–14a and 12b–14b are placed in the open or closed state in accordance with the state of control lines 16a and 16b, which may be referred to as INVERT and NOT INVERT, respectively. The switches 12a–14a are caused to close when the line 16a is active, while the switches 12b–14b are closed when the line 16b is active. The operation of the lines 16a–16b will be explained in greater detail hereinafter.

For purposes of example, however, initial conditions may be assumed wherein the line 16b is active, while positive current (with respect to the input terminals 10) is flowing through into the device. This current is then supplied through the switches 12b–14b, and is supplied to an amplifier 20 through a positive input lead 22 and a negative input lead 24. Each input lead 22 and 24 includes a resistor 26, which may for example be ten thousand ohms; the inputs to the amplifier 20 are coupled via a capacitor 27, which may for example be 0.01 microfarad. A variable resistor 28 is connected to provide feedback to the negative input of the amplifier 20, and is used for calibration.

The output of the amplifier 20 is then supplied to the negative input of an integrator 30 through a relatively large resistor 32, for example 1.4 Mohms, and a relatively smaller resistor 34, for example 10 Kohms. A feedback capacitor 36, which may for example have a value on the order of one microfarad, is connected between the output of the integrator 30 and the junction of the resistors 32 and 34. In a similar arrangement, a capacitor 38, preferably of the same value as the capacitor 36, and a resistor 40, preferably of the same value as the resistor 32, are connected between the positive input to the integrator 30 and a reference voltage 42. Thus the integrator 30 stores a charge corresponding to the input signal provided at the input terminals 10, irrespective of the polarity of the input signal. The amplifier 20 and the integrator 30 may each be low drift Type LH0044 integrated circuits as manufactured by National Semiconductor.

The output of the integrator 30 provides a positive input to a first comparator 50, and a negative input to a second comparator 52. The remaining input to the comparator 50 is provided from a reference circuit comprising three series-connected resistors 53, 54 and 56 between two voltage sources 42 and 58. The resistor 54 is preferably variable to ensure accuracy, and the slide arm thereof provides the negative input to the comparator 50. The positive input to the comparator 52 is similarly provided from three series connected resistors 59, 60 and 62 connected between a reference voltage 42 and a negative voltage source 64; the slide arm of the variable resistor 60 provides the positive input to the comparator 52. The reference inputs to the comparators 50 and 52 are preferably equal in magnitude but opposite in polarity. For example, the negative input to the comparator 50 may be 2.49 volts, while the positive input to the comparator 52 may be −2.49 volts.

When the output of the integrator 30 exceeds the reference input of one of the comparators 50 or 52, as for example when the integrator output reaches a magnitude of 2.50 volts, the output of one of the comparators goes high and provides a signal to one of two monostable multivibrators 70a or 70b (FIG. 1B). Assuming the initial conditions given above, the output of the comparator 50 will become active, which will in turn fire the multivibrator 70a. Pull up resistors 72 may be connected between the outputs of the comparators 50 and 52 and the voltage reference 64.

The output of the multivibrator 70a is provided to steering logic comprising a plurality of two-input nand gates 74a–74d, an RS flip flop 76 comprising cross-coupled nand gates 76a and 76b, an nand gate 78 and a JK flip flop 80 arranged as a divide-by-two stage. For the assumed initial conditions, wherein the NOT INVERT line 16b is active and the output of the comparator 50 goes active, the output of the nand gate 74d goes low and causes the output of the nand gate 76b to go high, providing an input signal to counter stages 82a, 82b, . . . , 82n. When the multivibrator 70a fires, the inverting output thereof also supplies a pulse to the nand gate 78, which causes a pulse to occur on the output of the nand gate 78. The output of the nand gate 78 fires one half of a dual Schmitt trigger 84, the output of which provides a clocking signal to the counter stages 82a–82n, thereby causing the counters to increment by one count. The output of the counters may be provided to a display or may be provided to control circuitry such as a device for terminating charging, or decoupling unnecessary loads in the event a state of substantial discharge has been reached.

At the same time, the output of the nand gate 78 provides a clock input to the flip flop 80, causing the signals on the lines 16a and 16b to be inverted; that is, the INVERT line goes active while the NOT INVERT line goes inactive. In this manner, the next integrator cycle will be performed in the opposite polarity, thereby cancelling out the effects of thermal drift and other circuit offsets, which tend to be of a single polarity. Thus substantially increased accuracy is provided. The output of the nand gate 78 also provides a reset signal on a line 90 to cause a plurality of solid state switches 92a, 92b and 92c (FIG. 1A) to close. The switch 92c is connected in parallel with the storage capacitor 38, such that closure of the switch dumps the charge stored thereon. Similarly, the switches 92a and 92b are connected in series and parallel to the storage capacitor 30 such that an active signal on the line 90 causes the capacitor 36 to be discharged. This readies the integrator for the next cycle.

To better understand the operation of the present invention during the inverted cycle, it will be apparent from the foregoing discussion that the input signal from the terminals 10 will now be provided to the amplifier 20 through the solid state switches 12a–14a, which reverses the polarity of the signal provided to the integrator 30. If the input signal continues to be of a positive polarity, the output of the comparator 52 goes active, causing the multivibrator 70b to fire. This places a low signal on the output of the nand gate 74c, leaving a high signal on the output of the nand gate 76b and triggering the nand gate 78 through the remaining input thereto. Retriggering the nand gate 78 fires the Schmitt trigger 84, incrementing the counter stages as before. Thus the reversal of polarity of the input signal causes errors to be minimized while still causing the counter to properly increment. The output of the nand gate 78 again triggers the flip flop 80, causing the NOT INVERT line to go active and restoring the system to the initial conditions initially described.

In the event the polarity of the input signal changes so as to reflect a discharging of the storage cells, the device of the present invention operates in a substantially similar manner except that the counter stages 82a–82n decrement instead of increment. Thus, for example, using the initial conditions given first above wherein the NOT INVERT line 16b was active, the negative polarity signal supplied to the integrator 30 would cause the comparator 52 to be tripped when the integrator output exceeded the preset threshold, thereby actuating the multivibrator 70b. This places a low signal on the output of the nand gate 74b, and resets the nand gate 76a, thereby resetting the RS flip flop 76. This places a low signal on the output of the nand gate 76b, causing the counter stages 82a–82n to decrement when the clock signal is provided by the Schmitt trigger 84. As before, the output of the nand gate 80 causes the state of the flip flop 80 to invert, causing a reversal of polarities at the integrator 30 during the next cycle, and also resets the storage capacitors 36 and 38. The nand gate 74a operates in a similar fashion if decrementing is required during the next integration cycle.

Having fully described one embodiment of the present invention, it is to be understood that numerous alternatives and equivalents which do not depart from the spirit of the present invention will be apparent to those skilled in the art given the teachings herein, and such alternatives and equivalents are intended to be included within the scope hereof.

I claim:

1. Apparatus for monitoring the amount of charge supplied by or to at least one storage battery comprising
input means adapted to receive an input signal representative of the current supplied by or to said at least one storage battery and for providing a signal proportional to said input signal,
integrator means responsive to said input means signal for integrating said signal to thereby develop an output signal representative of the charge supplied by or to said at least one storage battery,
threshold detection means responsive to said integrator means for detecting when the output signal of said integrator means exceeds a predetermined threshold,
means responsive to said threshold detection means for resetting said integrator means,
counter means responsive to said threshold detection means for indicating the charge available from said at least one storage battery, and
polarity inversion means responsive to said threshold detection means for inverting the polarity of said input means signal integrated by said integrator means when said integrator means is reset.

2. A method of determining the charge supplied by or to a storage battery including the steps of
receiving an input signal representative of the current supplied by or to said storage battery,
providing a signal proportional to said input signal to integrator means,
integrating the input signal by said integrator means and providing an integrated signal output,
detecting when the integrated signal output exceeds a predetermined threshold,
changing the count stored in a counter when the integrated signal output exceeds the predetermined threshold,
resetting the integrator means when the integrated signal output exceeds the predetermined threshold to begin a next integration cycle, and
inverting the polarity of the signal provided to said integrator means for the next integration cycle when the integrated signal output exceeds the predetermined threshold.

3. The invention of claim 1 wherein said input means includes means responsive to said polarity inversion means for inverting the polarity of said input means signal.

4. The invention of claim 1 wherein said threshold detection means is bipolar and includes a first comparator for establishing a positive polarity threshold and a second comparator for establishing a negative polarity threshold.

5. The invention of claim 3 wherein said integrator means includes precision amplifier means.

6. Apparatus for monitoring the amount of charge supplied by or to a storage battery comprising
input means adapted to receive an input signal representative of the current supplied by or to said storage battery,
polarity inversion means for providing an output proportional to said input signal at a first polarity and for providing said output at a second inverted polarity,
integrator means responsive to said polarity inversion means output for integrating said output to develop an output signal representative of the charge supplied by or to said storage battery,
threshold detection means responsive to said integrator means output signal for detecting when the integrator means output signal exceeds a predetermined threshold and for providing an output indication thereof,
means responsive to said threshold detection means output indication for resetting said integrator means, and
counter means for counting the threshold detection means output indications to indicate the charge available from said storage battery,
said polarity inversion means further for alternating said polarity inversion means output polarity between said first polarity and said second polarity in response to said threshold detection means output indication.

7. The invention of claim 6 wherein the polarity inversion means includes switching means for providing said polarity inversion means output at said first and second polarities.

8. The invention of claim 6 wherein said threshold detection means includes first comparator means for establishing a positive polarity threshold and second comparator means for establishing a negative polarity threshold.

9. The invention of claim 8 wherein said counter means is an up-down counter and said threshold detection means includes means for controlling the direction of the count of said counter means in accordance with the sequence of outputs from said first and second comparator means.

10. Apparatus for monitoring the amount of charge supplied by or to a storage battery comprising
input means adapted to receive an input signal representative of the current supplied by or to said storage battery,
switching means responsive to said input signal at said input means for providing an output proportional to said input signal at a first polarity and for providing said output at a second inverted polarity,
integrator means responsive to said switching means output for integrating said output to develop an output signal representative of the charge supplied by or to said storage battery,
bipolar threshold detection means including first comparator means for establishing a positive polarity threshold and for providing an output when said integrator exceeds said positive polarity threshold, and second comparator means for establishing a negative polarity threshold and for providing an output when said integrator output reaches said negative polarity threshold,
means responsive to said threshold detection means outputs for resetting said integrator means,
up-down counter means for counting said threshold means outputs, the direction of count of said up-down counter means being controled by the sequence of outputs from said threshold detection means, and
polarity inversion means responsive to said threshold detection means outputs for controlling said switching means to change said switching means output from said first polarity to said second polarity or from said second polarity to said first polarity each time said threshold detection means output occurs.

11. The method of claim 2 wherein the predetermined threshold comprises a positive polarity threshold and a negative polarity threshold.

12. A method of determining the charge supplied by or to a storage battery including the steps of
receiving an input signal representative of the current supplied by or to said storage battery,
providing a signal proportional to said input signal at a first polarity or at a second inverted polarity to integrator means,
integrating said signal by said integrator means to provide an integrated signal output,
detecting when the integrated signal output exceeds a predetermined threshold,
changing the count stored in a counter when the integrated signal output exceeds the predetermined threshold,
resetting said integrator means when the integrated signal output exceeds the predetermined threshold, and
alternating said signal proportional to said input signal between said first polarity and said second polarity in response to said integrated signal output exceeding the predetermined threshold.

13. The method of claim 12 wherein the predetermined threshold includes a positive polarity threshold and a negative polarity threshold.

14. The method of claim 13 wherein the step of changing the count further includes increasing or decreasing the count stored in the counter in accordance with the sequence that the integrated signal output exceeds said positive or negative polarity thresholds.

15. A method of determining the charge supplied by or to a storage battery including the steps of
receiving an input signal representative of the current supplied by or to said storage battery,
providing a signal proportional to said input signal at a first polarity or at a second inverted polarity to integrator means,
integrating said signal by said integrator means and providing an integrated signal output,
detecting when the integrated signal output exceeds a positive polarity threshold or a negative polarity threshold,
increasing or decreasing the count stored in a counter when the integrated signal output exceeds the positive or negative polarity threshold, said increasing or decreasing occurring in accordance with the sequence that the integrated signal output exceeds said positive or negative polarity threshold,
resetting said integrator means when the integrated signal output exceeds the positive or negative polarity thresholds, and
changing said signal proportional to said input signal from said first polarity to said second polarity or from said second polarity to said first polarity in response to said integrated signal output exceeding the predetermined threshold.

* * * * *